(12) United States Patent
Mollenkopf et al.

(10) Patent No.: US 10,233,164 B2
(45) Date of Patent: *Mar. 19, 2019

(54) ACESULFAME POTASSIUM COMPOSITIONS AND PROCESSES FOR PRODUCING SAME

(71) Applicant: Celanese International Corporation, Irving, TX (US)

(72) Inventors: Christoph Mollenkopf, Frankfurt am Main (DE); Peter Groer, Babenhausen (DE); Arvind Yadav, Hessen (IN)

(73) Assignee: Celanese International Corporation, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/014,471

(22) Filed: Jun. 21, 2018

(65) Prior Publication Data

US 2018/0297968 A1  Oct. 18, 2018

Related U.S. Application Data

(63) Continuation of application No. 15/704,356, filed on Sep. 14, 2017, now Pat. No. 10,029,998.

(60) Provisional application No. 62/397,484, filed on Sep. 21, 2016, provisional application No. 62/397,495, filed on Sep. 21, 2016.

(51) Int. Cl.
*C07D 291/06* (2006.01)
*A23L 27/30* (2016.01)

(52) U.S. Cl.
CPC ............ *C07D 291/06* (2013.01); *A23L 27/30* (2016.08); *A23L 27/31* (2016.08); *A23V 2002/00* (2013.01)

(58) Field of Classification Search
CPC .............................. C07D 209/06; A23L 27/30
USPC ....................................................... 544/200
See application file for complete search history.

(56) References Cited

U.S. PATENT DOCUMENTS

| | | |
|---|---|---|
| 4,563,521 A | 1/1986 | Clauss et al. |
| 4,607,100 A | 8/1986 | Clauss et al. |
| 4,638,063 A | 1/1987 | Clauss et al. |
| 4,695,629 A | 9/1987 | Clauss et al. |
| 4,804,755 A | 2/1989 | Reuschling et al. |
| 4,806,639 A | 2/1989 | Reuschling et al. |
| 4,876,341 A | 2/1989 | Reuschling et al. |
| 5,011,982 A | 4/1991 | Clauss et al. |
| 5,084,180 A | 1/1992 | Boateng |
| 5,103,046 A | 4/1992 | Clauss et al. |
| 5,334,397 A | 8/1994 | Ream et al. |
| 5,744,010 A | 4/1998 | Roscher et al. |
| 5,808,159 A | 9/1998 | Giebeler |
| 7,408,059 B2 | 8/2008 | Kobayashi et al. |
| 7,977,514 B2 | 7/2011 | Peters et al. |
| 8,182,756 B2 | 5/2012 | Liu et al. |
| 8,303,921 B2 | 11/2012 | Brietzke et al. |
| 8,309,048 B2 | 11/2012 | Brietzke et al. |
| 8,496,905 B2 | 7/2013 | Brietzke et al. |
| 8,658,830 B2 | 2/2014 | Brietzke et al. |
| 9,024,016 B2 | 5/2015 | Bayer et al. |
| 10,029,998 B2* | 7/2018 | Mollenkopf ............ A23L 27/30 |
| 2003/0065172 A1 | 4/2003 | Tian et al. |
| 2003/0065218 A1 | 4/2003 | Mollenkopf |
| 2008/0076919 A1 | 3/2008 | Liu et al. |
| 2009/0318685 A1 | 12/2009 | Saito et al. |
| 2009/0318686 A1 | 12/2009 | Saito et al. |
| 2010/0274057 A1 | 10/2010 | Peters et al. |
| 2011/0256045 A1 | 10/2011 | Brietzke et al. |
| 2011/0256046 A1 | 10/2011 | Brietzke et al. |
| 2013/0062192 A1 | 3/2013 | Brietzke et al. |
| 2013/0331565 A1 | 12/2013 | Bayer et al. |
| 2018/0079734 A1 | 3/2018 | Mollenkopf et al. |
| 2018/0079735 A1 | 3/2018 | Mollenkopf et al. |
| 2018/0079736 A1 | 3/2018 | Mollenkopf et al. |

FOREIGN PATENT DOCUMENTS

| | | |
|---|---|---|
| CA | 1273923 | 9/2009 |
| CN | 85104277 | 6/1985 |
| CN | 85104277 A | 12/1986 |
| CN | 1883790 | 12/2006 |
| CN | 200949088 | 9/2007 |
| CN | 101124981 | 2/2008 |

(Continued)

OTHER PUBLICATIONS

ASTM E 313-05, Standard Practice for Calculating Yellowness and Whiteness Indices from Instrumentally Measured Color Coordinates, Oct. 1, 2005, 6 pages.
Boehshar et al., 5-Chloroacesulfame K—a characteristic indicator for application of the "sulfur trioxide" process in the manufacture of acesulfame K, Research Disclosure, 2003, 477036.
Mayer et al., Acesulfame-K, Food Science and Technology, Jun. 28, 1991.
International Search Report in the corresponding International PCT Patent application No. PCT/US2007/051509, dated Nov. 9, 2017.
Linkies et al., Synthesis, 1990, 5, 405-406.
"Commission Direction 95/31/EC of Jul. 5, 1995 laying down specific criteria of purity concerning sweeteners for use in foodstuffs," Official Journal of the European Communities, Jul. 28, 1995, 19 pages.

(Continued)

*Primary Examiner* — Kahsay Habte
(74) *Attorney, Agent, or Firm* — Dority & Manning, P.A.

(57) ABSTRACT

Compositions and processes for producing high purity acesulfame potassium are described. One process comprises the steps of forming a cyclic sulfur trioxide adduct; hydrolyzing the cyclic sulfur trioxide adduct to form an acesulfame-H composition comprising acesulfame-H; neutralizing the acesulfame-H in the acesulfame-H composition to form a crude acesulfame potassium composition comprising acesulfame potassium and less than 2800 wppm acetoacetamide-N-sulfonic acid, wherein the neutralizing step is conducted or maintained at a pH at or below 11.0; and treating the crude acesulfame potassium composition to form the finished acesulfame potassium composition comprising acesulfame potassium and less than 37 wppm acetoacetamide-N-sulfonic acid.

26 Claims, 1 Drawing Sheet

(56) References Cited

FOREIGN PATENT DOCUMENTS

| | | |
|---|---|---|
| CN | 101124981 A | 2/2008 |
| CN | 101148300 | 3/2008 |
| CN | 101157666 | 4/2008 |
| CN | 101787001 | 7/2010 |
| CN | 101913898 | 12/2010 |
| CN | 201921689 | 8/2011 |
| CN | 102225333 | 10/2011 |
| CN | 102359926 | 2/2012 |
| CN | 102380226 | 3/2012 |
| CN | 102380266 A | 3/2012 |
| CN | 202221403 U | 5/2012 |
| CN | 102866042 | 1/2013 |
| CN | 103018368 | 4/2013 |
| CN | 103130743 | 6/2013 |
| CN | 10331294 | 10/2013 |
| CN | 103570592 | 2/2014 |
| CN | 103570592 A | 2/2014 |
| CN | 103588728 | 2/2014 |
| CN | 103588728 A | 2/2014 |
| CN | 103613566 | 3/2014 |
| CN | 103613566 A | 3/2014 |
| CN | 103960558 | 8/2014 |
| CN | 104193625 | 12/2014 |
| CN | 104209052 | 12/2014 |
| CN | 104225956 | 12/2014 |
| CN | 104292181 | 1/2015 |
| CN | 104292181 A | 1/2015 |
| CN | 204320227 | 5/2015 |
| CN | 105085160 A | 11/2015 |
| CN | 105111166 A | 12/2015 |
| CN | 105152446 | 12/2015 |
| CN | 105198778 | 12/2015 |
| CN | 106262665 | 1/2017 |
| CN | 106267879 | 1/2017 |
| CN | 106346138 | 1/2017 |
| CN | 106349009 | 1/2017 |
| CN | 106349190 | 1/2017 |
| CN | 106349191 | 1/2017 |
| CN | 106349300 | 1/2017 |
| CN | 106365952 | 2/2017 |
| CN | 106496159 A | 3/2017 |
| CN | 206001191 | 3/2017 |
| CN | 206001201 | 3/2017 |
| CN | 206001439 | 3/2017 |
| CN | 206121215 | 4/2017 |
| DE | 1249262 | 10/1966 |
| DE | 1268141 | 5/1968 |
| DE | 3522470 | 1/1987 |
| DE | 3531357 | 3/1987 |
| DE | 3545196 | 6/1987 |
| EP | 0155634 | 9/1985 |
| EP | 0159516 | 10/1985 |
| EP | 0215347 | 3/1987 |
| EP | 0217024 | 4/1987 |
| EP | 0218076 | 4/1987 |
| JP | 54032406 | 3/1979 |
| JP | S 5432406 A | 3/1979 |
| WO | WO93/19055 | 9/1993 |
| WO | WO 2011/133468 A1 | 10/2011 |
| WO | WO2013/182651 | 12/2013 |

OTHER PUBLICATIONS

"Commission Direction 2008/60/EC of Jun. 17, 2008 laying down specific purity criteria concerning sweeteners for use in foodstuffs," Official Journal of the European Union, Jun. 18, 2008, 40 pages.

"Regulations—Commission Regulation (EU) No. 231/2012 of Mar. 9, 2012 laying down specifications for food additives listed in Annexes II and II to Regulation (EC) No. 1333/2008 of the European Parliament and of the Council," Official Journal of the European Union, Mar. 22, 2012, 295 pages.

Opinion—"Re-evaluation of acesulfame K with reference to the previous SCF opinion of 1991," European Commission , Health & Consumer Protection Directorate-General, Directorate B—Scientific Health Opinions, Unit B3—Management of Scientific Committees II, Scientific Committee on Food, Mar. 13, 2000, 8 pages.

Product Information on "Acesulfame Potassium," 2001, 57th JECFA (joint FAO/WHO Expert Committee on Food Additives), FNP 52 Add 9, 2 pages.

Suenaga, "Ethylene-amine salt recovery—by converting the hydrochloride into the sulphate, and reacting with ammonia in aq. Solvent to ppte. Ammonium sulphate", WPI/Thompson, 1979, No. 16, XP 002598345 (See JP54032406).

Sunnett Brochure, "Acesulfame Potassium", Celanese, Apr. 2014.

Xiangsheng et al., "Synthesis of Acesulfame Potassium", Fine Chemicals, vol. 13, 1996, 1-15.

Information Disclosure Statement submitted Oct. 27, 2017, 2 pages.

Boehshar, Manfred & Burgard, Andreas. (2003). 5- Chloroacesulfame K—a characteristic indicator for application of the "sulfur trioxide" process in the manufacture of acesulfame K. Research Disclosure. 477036.

D. Mayer, et al., Acesulfame-K (Food Science and Technology), 1991, Intro., Chapters 15, 16, and 18, 56 pages.

\* cited by examiner

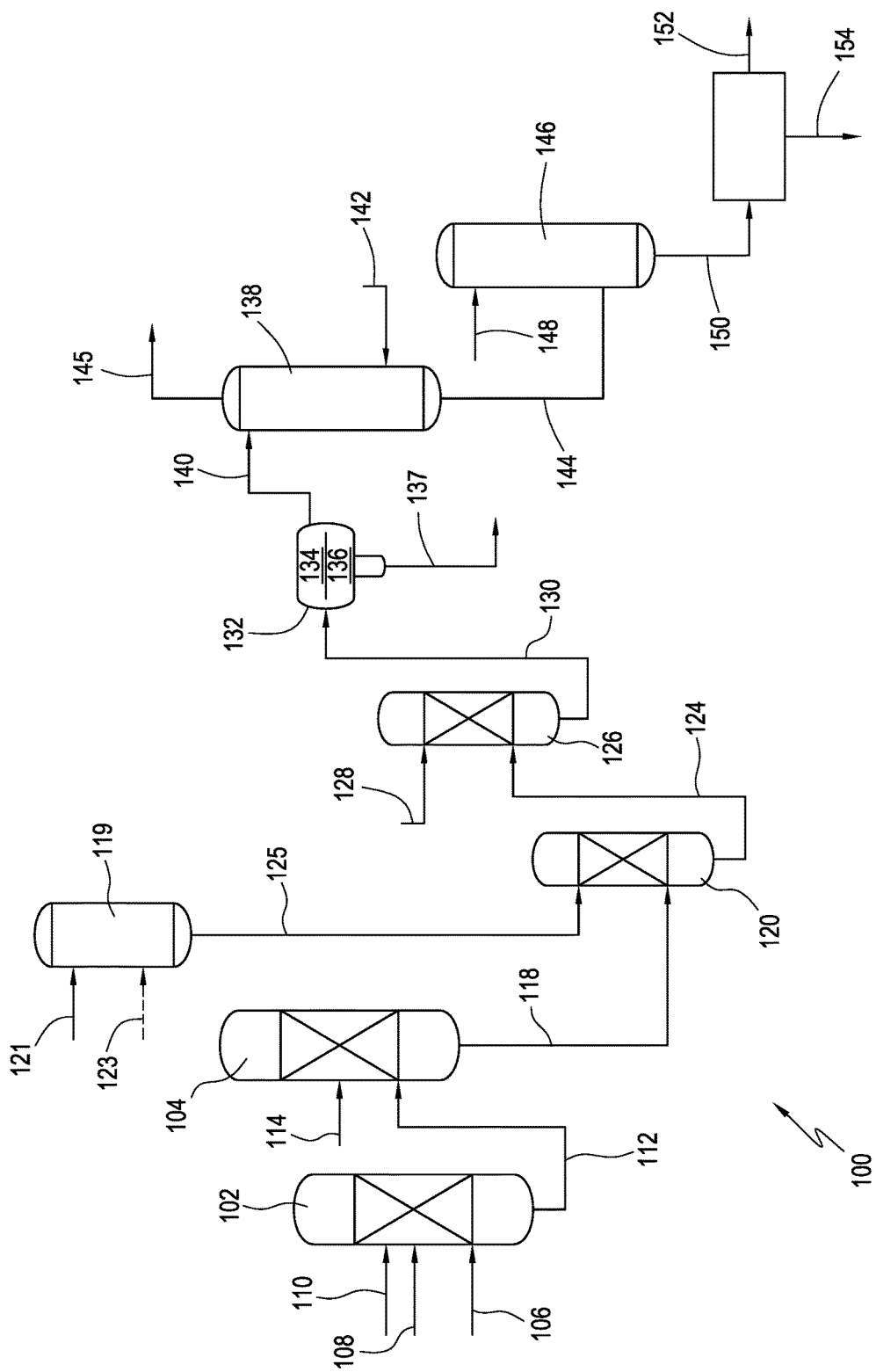

ACESULFAME POTASSIUM COMPOSITIONS AND PROCESSES FOR PRODUCING SAME

CROSS-REFERENCE TO RELATED APPLICATIONS

This application is a continuation of U.S. application Ser. No. 15/704,356 having a filing date of Sep. 14, 2017, which claims priority to U.S. Provisional Patent Application No. 62/397,484, filed Sep. 21, 2016, and to U.S. Provisional Patent Application No. 62/397,495, filed Sep. 21, 2016, the entireties of which are incorporated herein by reference.

FIELD OF INVENTION

The present invention relates generally to acesulfame potassium and to processes for producing acesulfame potassium. More specifically, the present invention relates to processes for producing high purity acesulfame potassium.

BACKGROUND OF THE INVENTION

Acesulfame potassium has an intense, sweet taste and has been used in many food-related applications as a sweetener. In conventional acesulfame potassium production processes, sulfamic acid and an amine, e.g., triethylamine, are reacted to form an amidosulfamic acid salt, such as a trialkyl ammonium amidosulfamic acid salt. The amidosulfamic acid salt is then reacted with diketene to form an acetoacetamide salt. The acetoacetamide salt may be cyclized, hydrolyzed, and neutralized to form acesulfame potassium. U.S. Pat. Nos. 5,744,010 and 9,024,016 disclose exemplary acesulfame potassium production processes.

Typically, the acetoacetamide salt intermediate is cyclized by reaction with sulfur trioxide in an inorganic or organic solvent to form a cyclic sulfur trioxide adduct. The solvent routinely utilized in this reaction is an organic solvent such as a halogenated, aliphatic hydrocarbon solvent, for example, dichloromethane. The adduct formed by this reaction is subsequently hydrolyzed and then neutralized with potassium hydroxide to form acesulfame potassium.

Acesulfame potassium product and the intermediate compositions produced by conventional methods contain undesirable impurities, such as acetoacetamide-N-sulfonic acid. Limits for the content of various impurities are often set by governmental regulations or customer guidelines. Separation of many of these impurities using standard purification procedures such as evaporation, crystallization, and/or filtration has proven difficult, resulting in consumer dissatisfaction and the failure to meet standards.

The need exists for improved processes for producing high purity acesulfame potassium compositions in which the formation of impurities such as acetoacetamide-N-sulfonic acid during synthesis is reduced or eliminated.

All of the references discussed herein are hereby incorporated by reference.

SUMMARY OF THE INVENTION

The application discloses processes for producing a finished acesulfame potassium composition, the processes comprising the steps of: forming a cyclic sulfur trioxide adduct; hydrolyzing the cyclic sulfur trioxide adduct to form an acesulfame-H composition comprising acesulfame-H; neutralizing the acesulfame-H in the acesulfame-H composition to form a crude acesulfame potassium composition; and treating the crude acesulfame potassium composition to form the finished acesulfame potassium composition comprising acesulfame potassium and less than 37 wppm acetoacetamide-N-sulfonic acid. The neutralizing step is preferably conducted or maintained at a pH at or below 11.0. The crude acesulfame potassium composition may comprise acesulfame potassium and less than 2800 wppm acetoacetamide-N-sulfonic acid. The neutralization step may comprise reacting acesulfame-H with a neutralizing agent, e.g., potassium hydroxide, in a acesulfame-H/neutralizing agent reaction mixture, to form the acesulfame potassium composition. The potassium hydroxide may be produced via a membrane process and the finished acesulfame potassium composition may comprise less than 10 wppm mercury. In some cases, the acesulfame-H/neutralizing agent reaction mixture comprises from 1 wt % to 95 wt % neutralizing agent and from 1 wt % to 95 wt % acesulfame-H, based on the total weight of the acesulfame-H/neutralizing agent reaction mixture. The neutralizing step may comprise neutralizing the acesulfame-H in the acesulfame-H composition to form the crude acesulfame potassium composition further comprising acetoacetamide. In some embodiments, the crude acesulfame potassium composition comprises from 500 wppm to 2375 wppm acetoacetamide-N-sulfonic acid and the finished acesulfame potassium composition comprises less than 25 wppm acetoacetamide-N-sulfonic acid and further comprises less than 25 wppm acetoacetamide. In one embodiment, the neutralizing step is conducted or maintained at a pH ranging from 9.0 to 11.0 and the crude acesulfame potassium composition comprises from 20 wppm to 2500 wppm acetoacetamide-N-sulfonic acid and the finished acesulfame potassium composition comprises less than 25 wppm acetoacetamide-N-sulfonic acid and less than 15 wppm acetoacetamide. In another embodiment, the neutralizing step is conducted or maintained at a pH ranging from 8 to 10.3 and the crude acesulfame potassium composition comprises from 600 wppm to 1200 wppm acetoacetamide-N-sulfonic acid, and the finished acesulfame potassium composition comprises less than 10 wppm acetoacetamide-N-sulfonic acid and less than 10 wppm acetoacetamide. In another embodiment, the neutralizing step is conducted or maintained at a pH ranging from 8 to 10.3 and the crude acesulfame potassium composition comprises less than 2400 wppm acetoacetamide-N-sulfonic acid, and the finished acesulfame potassium composition comprises less than 10 wppm acetoacetamide-N-sulfonic acid and less than 10 wppm acetoacetamide. The finished acesulfame potassium composition may comprise less than 37 wppm acetoacetamide, e.g., less than 20 wppm acetoacetamide. The neutralizing step may be conducted or maintained at a pH ranging from 9.0 to 11.0 and/or at a pH ranging from 9.0 to 10.5, e.g., from 8.0 to 10.3, and/or at a temperature below 90° C. The treating step may comprise an evaporating step with a residence time less than 180 minutes. Also disclosed is a process for producing a finished acesulfame potassium composition, the process comprising the steps of: reacting sulfamic acid and triethylamine to form an amidosulfamic acid salt; reacting the amidosulfamic acid salt and diketene to form acetoacetamide salt; contacting dichloromethane and a sulfur trioxide to form a cyclizing agent composition; reacting the acetoacetamide salt with sulfur trioxide in the cyclizing agent composition to form a cyclic sulfur trioxide adduct; hydrolyzing the cyclic sulfur trioxide adduct to form an acesulfame-H composition comprising acesulfame-H; neutralizing the acesulfame-H in the acesulfame-H to form a crude acesulfame potassium composition comprising acesulfame potassium and less than 2800 wppm acetoacetamide-N-sulfonic acid, wherein neutralizing step is conducted or maintained at a pH at or below 11.0; treating the crude acesulfame potassium composition to form the finished acesulfame potassium composition comprising acesulfame potassium and less than 37 wppm acetoacetamide-N-sulfonic acid. Preferably, steps (a), (b), and (c) are performed in any order before the performance of step (d). The neutralizing step may be conducted or maintained at a pH ranging from 9.0 to 11.0 and the crude acesulfame potassium composition may comprise from 20 wppm to 2500 wppm acetoacetamide-N-sulfonic acid and the finished acesulfame potassium composition may comprise less than 25 wppm acetoacetamide-N-sulfonic acid and less than 15 wppm acetoacetamide. The application also describes crude, intermediate, and finished acesulfame potassium composition produced by the processes described herein. In some cases, the application describes an acesulfame potassium composition comprising acesulfame potassium and less than 25 wppm acetoacetamide-N-sulfonic acid and less than 25 wppm acetoacetamide. In some cases, the acesulfame potassium composition further comprises 0.001 wppm to 5 wppm organic impurities and/or 0.001 wppm to 5 wppm of at least one heavy metal, e.g., the at least one heavy metal being selected from the group consisting of mercury, lead and mixtures thereof. In some cases, the acesulfame potassium composition further comprises mercury present in an amount of 1 wppb to 20 wppm and/or lead present in an amount of 1 wppb to 25 wppm.

BRIEF DESCRIPTION OF THE DRAWINGS

The invention is described in detail below with reference to the appended drawing.

FIG. 1 is a process flow sheet of an acesulfame potassium production process in accordance with one embodiment of the present invention.

DETAILED DESCRIPTION OF THE INVENTION

Introduction

Conventional processes for producing acesulfame potassium involve reacting sulfamic acid and an amine in the presence of acetic acid to form an amidosulfamic acid salt. The amidosulfamic acid salt is then reacted with an acetoacetylating agent, e.g., diketene, to form an acetoacetamide salt. The acetoacetamide salt is reacted with a cyclizing agent, e.g., sulfur trioxide, to form a cyclic sulfur trioxide adduct. The cyclic sulfur trioxide adduct is then hydrolyzed and neutralized via conventional means to form a crude acesulfame potassium composition comprising acesulfame potassium. This composition is phase separated into aqueous and organic phases. Most of the acesulfame potassium separates into the aqueous phase. As used herein, the term "crude acesulfame potassium composition" refers to the initial product of the neutralization step or to the aqueous phase that is formed from the phase separation step (without any further purification). The crude acesulfame potassium composition comprises at least 5 wt % acesulfame potassium. The crude acesulfame potassium composition may be optionally treated to form an "intermediate acesulfame potassium composition" and/or a "finished acesulfame potassium composition," which are discussed below.

Conventional acesulfame potassium compositions have been shown to comprise several undesirable impurities, among them acetoacetamide and acetoacetamide salts, e.g., acetoacetamide-N-sulfonate triethylammonium salt. Acetoacetamide-N-sulfonic acid and salts thereof may also be present. Content limits for these compounds in the finished acesulfame potassium composition are often determined by industry purity standards and/or by standards established for particular end use products that utilize acesulfame potassium as a sweetener. In some cases, limits for these impurities are determined by governmental regulations. For most applications, high acesulfame potassium purity levels are preferred. Thus, crude acesulfame potassium compositions typically are treated through various treatment operations to reduce the presence of these impurities. A non-limiting list of such treatment operations includes: evaporation, crystallization, and/or filtration.

Without being bound by theory, it has now been discovered that the neutralization of the hydrolyzed sulfur trioxide adduct may create stress, e.g., thermal stress, on acesulfame potassium molecules. This thermal stress may also affect acesulfame-H, also known as sweetener acid, which is formed during the hydrolysis step and is a precursor to the acesulfame potassium. This stress on the acesulfame potassium and potentially on the acesulfame-H can result in degradation of these compounds, resulting in the formation of undesirable impurities. In some situations, this stress may cause the acesulfame potassium/acesulfame-H to degrade into its formation reaction reactants, e.g., acetoacetamide and/or salts thereof and/or acetoacetamide-N-sulfonic acid, which can lead to the formation of additional impurities.

It has also now been discovered that the use of specific reaction parameters may advantageously reduce or eliminate stress on the acesulfame potassium (or acesulfame-H) and/or reduce or eliminate product degradation, which in turn reduces or eliminates the formation of additional impurities and ultimately leads to a high-purity end product.

In particular, conducting the neutralization step at within specific pH ranges or limits now has been found to surprisingly reduce or eliminate acesulfame potassium (or acesulfame-H) degradation and impurity formation, examples of which include the formation of acetoacetamide-N-sulfamic acid and/or the (re)formation of acetoacetamide salt. Traditionally, the neutralization step has been conducted or maintained at very high pH levels so as to maximize neutralization of the acesulfame-H to acesulfame potassium and minimize acesulfame-H content in the resultant crude acesulfame potassium composition. The reduced degradation of acesulfame potassium and acesulfame-H leads directly to the formation of the higher purity crude acesulfame potassium compositions, discussed herein, thereby simplifying subsequent treatment operations for forming the intermediate or finished acesulfame potassium compositions. The process also advantageously leads to the formation of intermediate and finished acesulfame potassium compositions having low acetoacetamide-N-sulfamic acid and/or acetoacetamide content.

In addition to the stress formed during the neutralization step, the treatment operations employed to remove impurities from the acesulfame potassium in the crude acesulfame potassium composition may also result in stress, e.g., thermal stress, on the acesulfame potassium itself (or the acesulfame-H), which also may result in degradation. It is believed that under such stress, acetoacetamide-N-sulfamic acid may degrade (and optionally hydrolyze) into acetoacetamide and N-sulfonic acid (and optionally N-sulfonic acid derivatives). Thus, thermal stress in the treatment operations may lead to the formation of additional undesirable byproducts, e.g., acetoacetamide. Advantageously, the reduction in the content of acetoacetamide-N-sulfamic acid in the crude acesulfame potassium composition further provides for accompanying reductions in acetoacetamide content that may be formed in subsequent treatment operations, which leads to improved efficiencies and, ultimately, to reduced acetoacetamide content in the resultant finished acesulfame potassium composition.

Additional specific terms that are used herein are now defined. "Acetoacetamide," as used herein, refers to the following molecule:

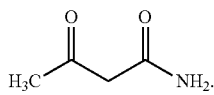

"Acetoacetamide-N-sulfonic acid" as used herein, refers to the molecule shown below. In some cases, acetoacetamide-N-sulfonic acid may be a degradation product of acesulfame potassium or acesulfame-H. The term "acetoacetamide-N-sulfonic acid," as used herein, also includes salts of acetoacetamide-N-sulfamic acid, e.g., potassium, sodium, and other alkali metal salts.

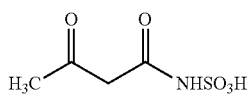

Crude acesulfame compositions may be treated to form intermediate acesulfame potassium compositions and finished acesulfame compositions, and this treatment step may include one or more concentrating or separating operations.

An "intermediate acesulfame potassium composition" refers to a composition resulting from the concentrating of the crude acesulfame potassium composition, e.g., the removal of water from the crude acesulfame potassium composition. The intermediate acesulfame potassium composition comprises at least 10 wt % acesulfame potassium, based on the total weight of the intermediate acesulfame potassium composition, and has an acesulfame potassium weight percentage that is higher than that of the crude acesulfame potassium composition.

A "finished acesulfame potassium composition" refers to a composition (preferably directly) resulting from the separating, e.g., crystallizing and/or filtering, of the intermediate acesulfame potassium composition. The finished acesulfame potassium composition comprises at least 15 wt % acesulfame potassium, based on the total weight percentage of the finished acesulfame potassium composition, and has an acesulfame potassium weight percentage that is higher than that of the intermediate acesulfame potassium composition.

"Residence time," as used herein, refers to the time period that a composition (or stream) to be treated, e.g., a crude acesulfame potassium composition, remains in a particular treatment operation. Residence time begins when the composition to be treated enters the treatment operation, and residence time ends when the resultant compositions (formed via the treatment) exit the treatment operation. As one particular example, residence time for a concentrating operation, e.g., evaporation, refers to the time from when a crude acesulfame potassium composition enters the evaporator until the intermediate acesulfame potassium composition exits the evaporator. As another example, residence time for a separating operation, e.g., crystallization, refers to the time from when a crude acesulfame potassium composition enters the crystallizer until the intermediate acesulfame potassium composition exits the crystallizer.

"Cyclization reaction time," as used herein, refers to the time from the start of the acetoacetamide salt feed to the termination of the acetoacetamide salt feed. In some cases, if indicated, the cyclization reaction time may include additional time past the termination of the acetoacetamide salt feed, e.g., an extra 5 minutes or an extra minute.

The treatment of the crude acesulfame potassium composition may entail one or more operations, e.g., a concentrating operation and/or a separating operation. Generally, a concentrating operation is not considered a separating operation. In some embodiments, the concentrating operation(s) and the separating operation(s) make up the overall treatment of the crude acesulfame potassium composition, which results in the finished acesulfame potassium composition. In some cases, the overall concentrating operation may include multiple individual concentrating operations or units and the overall separating operation may include multiple individual separating operations or units.

"Wppm" and "wppb," as used herein, mean weight parts per million or weight parts per billion, respectively, and are based on the total weight of the entire respective composition, e.g., the total weight of the entire crude acesulfame potassium composition or the entire finished acesulfame potassium composition.

Acesulfame Potassium Formation (pH Control)

Processes for producing high purity acesulfame potassium compositions are described herein. In one embodiment, the process comprises the steps of forming a cyclic sulfur trioxide adduct, hydrolyzing the cyclic sulfur trioxide adduct to form an acesulfame-H composition comprising acesulfame-H, and neutralizing the acesulfame-H in the acesulfame-H composition (and optionally phase separating the neutralization reaction product) to form a crude acesulfame potassium composition. The crude acesulfame potassium composition comprises acesulfame potassium and impurities, e.g., acetoacetamide-N-sulfonic acid, present in extremely low amounts, if at all.

Other impurities may also be formed in the aforementioned process steps. For example, the formation of the cyclic sulfur trioxide adduct may yield a cyclic sulfur trioxide adduct composition that comprises the cyclic sulfur trioxide adduct and additional reaction side products and impurities. Similarly, the formation of the acesulfame-H may yield an acesulfame-H composition that comprises acesulfame-H and additional reaction side products and impurities.

The formation of the cyclic sulfur trioxide adduct may comprise the steps of reacting sulfamic acid and triethylamine to form an amidosulfamic acid salt; reacting the amidosulfamic acid salt and diketene to form acetoacetamide salt; contacting solvent, e.g., dichloromethane, and cyclizing agent, e.g., sulfur trioxide, to form a cyclizing agent composition; and reacting the acetoacetamide salt with sulfur trioxide in the cyclizing agent composition to form a cyclic sulfur trioxide adduct. The amidosulfamic acid salt formation reaction, the acetoacetamide salt formation reaction, and the contacting of the solvent and the cyclizing agent may be performed in any order as long as these steps are performed prior to the reaction of the acetoacetamide salt with cyclizing agent in the cyclizing agent composition.

As noted above, in the neutralization step, a neutralizing agent neutralizes the acesulfame-H to form acesulfame potassium. Importantly, the neutralization step is conducted or maintained at low pH levels and/or the pH of the neutralization step is maintained at low levels, which results in reduction or elimination of the formation of certain impurities, e.g., acetoacetamide-N-sulfonic acid, in the crude acesulfame potassium composition. In this context, "conducted" means that the neutralization step begins at a low pH level, and "maintained" means that steps are taken to ensure that the pH stays within a low pH range throughout the entire neutralization step.

In one embodiment, the neutralization step is conducted or maintained at a pH at or below 11.0, e.g., at or below 10.5, at or below 10, at or below 9.5, at or below 9.0, at or below 8.5, at or below 8.0, at or below 7.5, at or below 7.0, or at or below 6.5. In some embodiments, the pH of the neutralization step is conducted or maintained below the aforementioned limits (the limit itself is not included). In terms of ranges, the neutralization step is preferably conducted or maintained at a pH ranging from 6.0 to 11.0, e.g., from 7.0 to 11.0, from 7.5 to 11.0, from 9.0 to 11.0, from 9 to 10.5, from 7.0 to 10.5, from 7.0 to 10.0, from 8 to 10.5, from 8 to 10.3, from 8 to 10, or from 7.5 to 9.0. The pH of the neutralization step is preferably conducted or maintained within the aforementioned ranges (the endpoints are not included).

In preferred embodiments, the neutralizing step comprises reacting the acesulfame-H in the acesulfame-H composition with a neutralizing agent to form the acesulfame potassium composition.

The utilization of these pH ranges and limits provides for excellent conversion of acesulfame-H to acesulfame potassium while minimizing the content of acesulfame-H and acesulfame potassium degradation products in the resultant crude acesulfame potassium composition (and the finished acesulfame potassium composition). Although low pH levels are generally desired according to embodiments of the invention, it has now been discovered that if the pH of the neutralization step is too low, acesulfame-H conversion to acesulfame potassium may be undesirebly reduced. If the pH of the neutralization step is too high, the acesulfame potassium degrades into unwanted by-products. Acesulfame-H is known to be less stable than acesulfame potassium, and as such, more susceptible to degradation. By using the aforementioned pH ranges and limits, fewer acesulfame-H molecules degrade into its precursors, e.g., acetoacetamide, while ensuring formation of acesulfame potassium. In addition to the reduced acetoacetamide-N-sulfonic acid levels in the crude acesulfame potassium composition, the low pH levels may also have a beneficial effect on other impurities that may be formed downstream of the neutralization step. For example, by reducing acetoacetamide-N-sulfonic acid content, the formation of its decomposition byproducts is also reduced during the evaporation and/or the crystallization steps.

The neutralizing agent preferably comprises a potassium-containing compound. Preferably the neutralizing agent comprises potassium hydroxide. Other suitable examples of neutralizing agents include $KHCO_3$, $K_2CO_3$, and potassium alcoholates. In preferred embodiments, the neutralizing agent comprises a base, e.g., a hydroxide compound. In cases where potassium hydroxide is employed, the potassium hydroxide may be produced via a membrane process. Alternatively, the potassium hydroxide may be produced via an amalgam process.

The specific method employed to maintain the pH within the desired range in the neutralizing step may vary widely. In some embodiments, the pH in the neutralizing step is conducted or maintained within the desired range by controlling the amount of neutralizing agent, preferably a basic compound, e.g., a hydroxide, utilized in the neutralizing step. In one embodiment, when a continuous process is employed, the pH of the neutralizing step is the pH at which the continuous process is maintained. In one embodiment, when a batch process is employed, the pH of the neutralizing step is the final pH of the neutralization reaction mixture, e.g., at the completion of the batch operation.

In some cases, the pH in the neutralizing step may be maintained within the desired range by managing the components of the neutralization reaction mixture, which comprises acesulfame-H and neutralizing agent (and also solvent). For example, the composition of the neutralization reaction mixture may include from 1 wt % to 95 wt % neutralizing agent, e.g., from 10 wt % to 85 wt % or from 25 wt % to 75 wt %, and from 1 wt % to 95 wt % acesulfame-H, e.g., from 10 wt % to 85 wt % or from 25 wt % to 75 wt %. These concentration ranges are based on the mixture of neutralization agent and acesulfame-H (not including solvent).

In some embodiments, the temperature at which the treatment of the crude acesulfame potassium composition is conducted is maintained at a low level. Also, in some embodiments, the residence time (of the crude acesulfame potassium composition or a derivative thereof) in one or more operations of the treatment process) is maintained at a low level. The employment of the treatment under these parameters advantageously reduces/eliminates decomposition of acetoacetamide-N-sulfonic acid into other impurities.

In some embodiments, the treatment of the crude acesulfame potassium composition, e.g., one or more of the steps that make up the treatment operation, is conducted at or maintained at a low temperature. Preferably the treatment operation comprises a concentrating operation and a separating operation and these operations are conducted at low temperature.

In some embodiments, the concentrating operation, e.g., one or more of the steps that make up the concentrating operation, is conducted at or maintained at a low temperature, e.g., a temperature below 90° C., e.g., below 88° C., below 85° C., below 83° C., below 80° C., below 78° C., below 75° C., below 73° C., below 70° C., below 65° C., below 55° C., below 50° C., or below 46° C. In some cases, the temperature of the concentrating operation may be maintained at a temperature above 0° C., e.g., above 10° C., above 15° C., above 20° C., above 22° C., above 25° C., above 35° C., above 40° C. or above 50° C. In terms of ranges, the temperature of the concentrating operation may range from 0° C. to 90° C., e.g., 25° C. to 90° C., from 55° C. to 90° C., from 10° C. to 88° C., from 10° C. to 85° C., from 75° C. to 88° C., from 80° C. to 88° C., from 15° C. to 85° C., from 75° C. to 85° C., from 20° C. to 83° C., from 20° C. to 80° C., from 22° C. to 78° C., from 25° C. to 75° C., from 25° C. to 73° C., from 15° C. to 50° C., from 25° C. to 65° C., from 22° C. to 50° C., from 20° C. to 55° C., from 25° C. to 70° C., or from 30° C. to 60° C.

In some embodiments, the separating operation, e.g., one or more of the steps that make up the separating operation, is conducted at or maintained at a low temperature, e.g., a temperature below 35° C., below 30° C., below 25° C., below 20° C., below 15° C., below 10° C., below 8° C., below 6° C., below 5° C., or below 0° C. In some cases, the temperature of the separating operation may be maintained at a temperature above −25° C., e.g., above −10° C., above 0° C., above 5° C., above 10° C., above 15° C., above 25° C., or above 30° C. In terms of ranges, the temperature of the separating operation may range from −25° C. to 35° C., e.g., −10° C. to 35° C., from 0° C. to 35° C., from 5° C. to 30° C., from −10° C. to 30° C., from −10° C. to 25° C., from −10° C. to 20° C., from −10° C. to 15° C., from 0° C. to 25° C., or from −10° C. to 30° C. The employment of the aforementioned temperatures in the treatment advantageously improves final product purity.

In some embodiments, the treatment of the crude acesulfame potassium composition, e.g., one or more of the steps that make up the treatment operation, is conducted at or maintained at a low residence time. Preferably the treatment operation comprises a concentrating operation and a separating operation and these operations are conducted at a low residence time and/or pH.

In some embodiments, the concentrating operation, e.g., one or more of the steps that make up the concentrating operation, is conducted at or maintained at a low residence time. In one embodiment, residence time is less than 180 minutes, e.g., less than 170 minutes, less than 150 minutes, less than 120 minutes, less than 100 minutes, less than 90 minutes, less than 75 minutes, less than 50 minutes, less than 40 minutes, less than 30 minutes, less than 20 minutes, or less than 10 minutes. In terms of lower limits, residence time may be at least 1 second, e.g., at least 10 seconds, at least 1 minute, at least 10 minutes, or at least 15 minutes. In terms of ranges, the residence time may range from 1 second to 180 minutes, e.g., from 10 seconds to 180 minutes, from 1 minute to 180 minutes, from 10 minutes to 150 minutes, from 1 minute to 50 minutes, from 1 minute to 30 minutes, from 10 minutes to 100 minutes, from 1 minute to 80 minutes, from 10 minutes to 80 minutes, from 10 minutes to 50 minutes, from 15 minutes to 90 minutes, or from 15 minutes to 75 minutes. The same residence time limits and ranges are applicable to the separating operation, e.g., one or more of the steps that make up the separating operation. The employment of residence times in the concentrating operation and/or separating operation advantageously improves final product purity.

In some embodiments, the concentrating operation, e.g., one or more of the steps that make up a concentrating operation, is conducted at or maintained at a low pH. In one embodiment, the pH of the separating is maintained below 10.0, e.g., below 9.5, below 9.0, below 8.5, below 8.0, below 7.5, below 7.0, or below 6.5. In terms of ranges, the pH of the concentrating operation is preferably maintained between 6.0 and 10.0, e.g., between 6.5 and 9.5, between 7.0 and 9.0, or between 7.5 and 8.5. The same pH limits and ranges are applicable to the separating operation, e.g., one or more of the steps that make up the separating operation. The employment of low pH levels in the concentrating operation or separating operation advantageously improves final product purity.

The finished acesulfame potassium composition formed via the process(es) described herein will have high purity.

Acesulfame Potassium Compositions

The crude acesulfame potassium composition is formed by hydrolyzing a cyclic sulfur trioxide adduct to form an acesulfame-H composition and neutralizing the acesulfame-H in the acesulfame-H composition to form the crude acesulfame potassium composition, as discussed herein. The product of the neutralization step is phase separated into aqueous and organic phases. The crude acesulfame potassium composition may be obtained from the aqueous phase (without any further purification). The crude acesulfame potassium composition comprises a mixture of acesulfame potassium and acetoacetamide-N-sulfonic acid, e.g., less than 2800 wppm acetoacetamide-N-sulfonic acid, e.g., less than 2700, less than 2600 wppm, less than 2500 wppm, less than 2400 wppm, less than 2000 wppm, less than 1500 wppm, less than 1000 wppm, less than 500 wppm, or less than 100 wppm. In terms of ranges, the crude acesulfame potassium composition may comprise from 1 wppm to 2800 wppm acetoacetamide-N-sulfonic acid, e.g., from 1 wppm to 2700 wppm, from 10 wppm to 2700 wppm, from 20 wppm to 2500 wppm, from 100 wppm to 2500 wppm, from 500 wppm to 2500 wppm, from 1500 to 2400 wppm, from 500 wppm to 2375 wppm, from 600 wppm to 2000 wppm, from 900 to 1900 wppm, from 300 wppm to 1500 wppm, from 400 wppm to 1400 wppm, from 600 wppm to 1200 wppm, or from 700 wppm to 1100 wppm.

The crude acesulfame potassium composition may further comprise acetoacetamide, which may be present in the amounts discussed above with respect to acetoacetamide-N-sulfonic acid.

The finished acesulfame potassium compositions, which are typically suitable for end consumer usage, are formed by treating the crude acesulfame potassium composition to remove impurities. In some cases, the finished acesulfame potassium composition is typically the product that is sold. This finished acesulfame potassium composition preferably comprises a mixture of acesulfame potassium and less than 37 wppm acetoacetamide, e.g., less than 35 wppm, less than 30 wppm, less than 25 wppm, less than 20 wppm, less than 15 wppm, less than 12 wppm, less than 10 wppm, less than 7 wppm, less than 5 wppm, less than 3 wppm, less than 1 wppm, less than 0.8 wppm, less than 0.5 wppm, or less than 0.3 wppm. In some cases the finished acesulfame potassium composition is free of acetoacetamide, e.g., substantially free of acetoacetamide (undetectable). In terms of ranges, the finished acesulfame potassium composition may comprise from 1 wppb to 37 wppm acetoacetamide, e.g., from 10 wppb to 35 wppm, from 10 wppb to 25 wppm, from 10 wppb to 15 wppm, from 10 wppb to 12 wppm, from 10 wppb to 10 wppm, from 10 wppb to 7 wppm, from 10 wppb to 5 wppm, from 10 wppb to 3 wppm, from 100 wppb to 15 wppm, from 100 wppb to 10 wppm, or from 100 wppb to 5 wppm.

The finished acesulfame potassium composition preferably comprises a mixture of acesulfame potassium and less than 37 wppm acetoacetamide-N-sulfonic acid, e.g., less than 35 wppm, less than 30 wppm, less than 25 wppm, less than 20 wppm, less than 15 wppm, less than 12 wppm, less than 10 wppm, less than 7 wppm, less than 5 wppm, less than 3 wppm, less than 1 wppm, less than 0.8 wppm, less than 0.5 wppm, or less than 0.3 wppm. In some cases the finished acesulfame potassium composition is free of acetoacetamide-N-sulfonic acid, e.g., substantially free of acetoacetamide-N-sulfonic acid (undetectable). In terms of ranges, the finished acesulfame potassium composition may comprise from 1 wppb to 37 wppm acetoacetamide-N-sulfonic acid, e.g., from 10 wppb to 35 wppm, from 10 wppb to 25 wppm, from 10 wppb to 15 wppm, from 10 wppb to 12 wppm, from 10 wppb to 10 wppm, from 10 wppb to 7 wppm, from 10 wppb to 5 wppm, from 10 wppb to 3 wppm, from 100 wppb to 15 wppm, from 100 wppb to 10 wppm, or from 100 wppb to 5 wppm.

The acetoacetamide-N-sulfonic acid and/or the acetoacetamide content may be measured in the crude, intermediate, or finished acesulfame potassium compositions via high performance liquid chromatography (HPLC) analysis, based on European Pharmacopoeia guidelines for thin layer chromatography (2017) and adapted for HPLC. A particular measurement scenario utilizes an LC Systems HPLC unit from Shimadzu having a CBM-20 Shimadzu controller and being equipped with an IonPac NS1 ((5 μm) 150×4 mm) analytical column and an IonPac NG1 guard column (35×4.0 mm). A Shimadzu SPD-M20A photodiode array detector can be used for detection (at 270 nm and 280 nm wavelength). Analysis may be performed at 23° C. column temperature. As a first eluent solution, an aqueous mixture of tetra butyl ammonium hydrogen sulfate (3.4 g/L), acetonitrile (300 mL/L), and potassium hydroxide (0.89 g/L) may be employed; as a second eluent solution, an aqueous mixture of tetra butyl ammonium hydrogen sulfate (3.4 g/L) and potassium hydroxide (0.89 g/L) may be employed. Elution may be conducted in gradient mode according to the following second eluent flow profile:

0 to 3 minutes: constant 80% (v/v)
3 to 6 minutes: linear reduction to 50% (v/v)
6 to 15 minutes: constant at 50% (v/v)
15 to 18 minutes: linear reduction to 0%
18 to 22 minutes: constant at 0%
22 to 24 minutes: linear increase to 80% (v/v)
24 to 35 minutes constant at 80% (v/v).

Overall flow rate of eluent may be approximately 1.2 mL/min. The data collection and calculations may be performed using Lab Solution software from Shimadzu.

As noted above, the crude acesulfame potassium composition is formed by the aforementioned reactions, hydrolysis, and neutralization and the finished acesulfame potassium composition is formed by treatment of the crude acesulfame potassium composition. In preferred embodiments, the neutralizing may be conducted or maintained at a pH at or below 11.0, e.g., at or below 10.5, at or below 10, at or below 9.5, at or below 9.0, at or below 8.5, at or below 8.0, at or below 7.5, at or below 7.0, or at or below 6.5. (optionally at a pH ranging from 7.5 to 11, e.g., from 9.0 to 11.0, from 9 to 10.5, from 7.0 to 10.5, from 7.0 to 10.0, from 8 to 10.5, from 8 to 10.3, from 8 to 10, or from 7.5 to 9.0); the crude acesulfame potassium composition may comprise less than 2800 acetoacetamide-N-sulfonic acid, e.g., less than 2700 wppm, less than 2600 wppm, less than 2500 wppm, less than 2400 wppm, less than 2000 wppm, less than 1500 wppm, less than 1000 wppm, less than 500 wppm, or less than 100 wppm (optionally from 1 wppm to 2800 wppm acetoacetamide-N-sulfonic acid, e.g., from 1 wppm to 2800 wppm, from 10 wppm to 2700 wppm, from 20 wppm to 2500 wppm, from 100 wppm to 2500 wppm, from 500 wppm to 2500 wppm, from 1500 to 2400 wppm, from 500 wppm to 2375 wppm, from 600 wppm to 2000 wppm, from 900 to 1900 wppm, from 300 wppm to 1500 wppm, from 400 wppm to 1400 wppm, from 600 wppm to 1200 wppm or from 700 wppm to 1100 wppm); and the finished acesulfame potassium composition may comprise less than 37 wppm acetoacetamide-N-sulfonic acid, e.g., less than 35 wppm, less than 30 wppm, less than 25 wppm, less than 20 wppm, less than 15 wppm, less than 12 wppm, less than 10 wppm, less than 7 wppm, less than 5 wppm, less than 3 wppm, less than 1 wppm, less than 0.8 wppm, less than 0.5 wppm, or less than 0.3 wppm (optionally from 1 wppb to 37 wppm acetoacetamide-N-sulfonic acid, e.g., from 10 wppb to 35 wppm, from 10 wppb to 25 wppm, from 10 wppb to 15 wppm, from 10 wppb to 12 wppm, from 10 wppb to 10 wppm, from 10 wppb to 7 wppm, from 10 wppb to 5 wppm, from 10 wppb to 3 wppm, from 100 wppb to 15 wppm, from 100 wppb to 10 wppm, or from 100 wppb to 5 wppm); and less than 37 wppm acetoacetamide, e.g., less than 35 wppm, less than 30 wppm, less than 25 wppm, less than 20 wppm, less than 15 wppm, less than 12 wppm, less than 10 wppm, less than 7 wppm, less than 5 wppm, less than 3 wppm, less than 1 wppm, less than 0.8 wppm, less than 0.5 wppm, or less than 0.3 wppm (optionally from 10 wppb to 37 wppm acetoacetamide, e.g., from 10 wppb to 35 wppm, from 10 wppb to 15 wppm, from 10 wppb to 12 wppm, from 10 wppb to 10 wppm, from 10 wppb to 7 wppm, from 10 wppb to 5 wppm, from 10 wppb to 3 wppm, from 100 wppb to 15 wppm, from 100 wppb to 10 wppm, or from 100 wppb to 5 wppm).

In a particular embodiment, the crude acesulfame potassium composition comprises from 500 wppm to 2375 wppm acetoacetamide-N-sulfonic acid and the finished acesulfame potassium composition comprises less than 25 wppm acetoacetamide-N-sulfonic acid and further comprises less than 25 wppm acetoacetamide.

In another particular embodiment, the neutralizing is conducted or maintained at a pH ranging from 9.0 to 11.0, the crude acesulfame potassium composition comprises from 20 wppm to 2500 wppm acetoacetamide-N-sulfonic acid, and the finished acesulfame potassium composition comprises less than 25 wppm acetoacetamide-N-sulfonic acid and less than 15 wppm acetoacetamide.

In another particular embodiment, the neutralizing is conducted or maintained at a pH ranging from 8.0 to 10.3 and the crude acesulfame potassium composition comprises from 600 wppm to 1200 wppm acetoacetamide-N-sulfonic acid, and the finished acesulfame potassium composition comprises less than 10 wppm acetoacetamide-N-sulfonic acid and less than 10 wppm acetoacetamide.

In another particular embodiment, the neutralizing is conducted or maintained at a pH ranging from 8 to 10.3, the crude acesulfame potassium composition comprises less than 2400 wppm acetoacetamide-N-sulfonic acid, and the finished acesulfame potassium composition comprises less than 10 wppm acetoacetamide-N-sulfonic acid and less than 10 wppm acetoacetamide.

In another particular embodiment, the neutralizing is conducted or maintained at a pH ranging from 9.0 to 11.0, the crude acesulfame potassium composition comprises from 500 wppm to 2375 wppm acetoacetamide-N-sulfonic acid, and the finished acesulfame potassium composition comprises from 10 wppb to 10 wppm acetoacetamide-N-sulfonic acid and from 10 wppb to 10 wppm acetoacetamide.

The acesulfame potassium compositions (crude and/or finished) may, in some cases, comprise other impurities. Exemplary impurities include, inter alia, halo-acesulfame potassium. The acesulfame potassium compositions (crude and/or finished) also may comprise heavy metals. The organic impurities and/or heavy metals may be present in an amount ranging from 1 wppb to 25 wppm, based on the total weight of the respective acesulfame potassium composition, crude or finished, e.g., from 100 wppb to 20 wppm, from 100 wppb to 15 wppm, from 500 wppb to 10 wppm, or from 1 wppm to 5 wppm. Heavy metals are defined as metals with relatively high densities, e.g., greater than 3 g/cm$^3$ or greater than 7 g/cm$^3$. Exemplary heavy metals include lead and mercury. In some cases, the crude or finished acesulfame potassium composition may comprise mercury in an amount ranging from 1 wppb to 25 wppm, e.g., from 100 wppb to 20 wppm, from 100 wppb to 15 wppm, from 500 wppb to 10 wppm, or from 1 wppm to 5 wppm. In terms of limits, the crude or finished acesulfame potassium composition may comprise less than 25 wppm mercury, e.g., less than 20 wppm, less than 15 wppm, less than 10 wppm, or less than 5 wppm. In some cases, the crude or finished acesulfame potassium composition may comprise lead in an amount ranging from 1 wppb to 25 wppm, e.g., from 100 wppb to 20 wppm, from 100 wppb to 15 wppm, from 500 wppb to 10 wppm, or from 1 wppm to 5 wppm. In terms of limits, the crude or finished acesulfame potassium composition may comprise less than 25 wppm lead, e.g., less than 20 wppm, less than 15 wppm, less than 10 wppm, or less than 5 wppm. In some cases, when potassium hydroxide is formed via a membrane process, the resultant crude or finished acesulfame potassium composition may have very low levels of mercury, if any, e.g., less than 10 wppm, less than 5 wppm, less than 3 wppm, less than 1 wppm, less than 500 wppb, or less than 100 wppb.

Intermediate Reaction Parameters

The reactions for production of high purity acesulfame potassium are described in more detail as follows.

Amidosulfamic Acid Salt Formation Reaction

In a first reaction step, sulfamic acid and an amine are reacted to form sulfamic acid salt. An exemplary reaction scheme that employs triethylamine as the amine and yields triethyl ammonium sulfamic acid salt is shown in reaction (1), below.

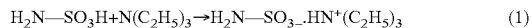
(1)

Acetic acid is also present in the first reaction mixture and reacts with the amine, e.g., triethylamine, to form a triethylammonium acetate, as shown in reaction (2), below.

(2)

The amine employed in these reactions may vary widely. Preferably, the amine comprises triethylamine. In one embodiment, the amine may be selected from the group consisting of trimethylamine, diethylpropylamine, tri-n-propylamine, triisopropylamine, ethyldiisopropylamine, tri-n-butylamine, triisobutylamine, tricyclohexylamine, ethyldicyclohexylamine, N,N-dimethylaniline, N,N-diethylaniline, benzyldimethylamine, pyridine, substituted pyridines such as picoline, lutidine, cholidine or methylethylpyridine, N-methylpiperidine, N-ethylpiperidine, N-methylmorpholine, N,N-dimethylpiperazine, 1,5-diazabicyclo[4.3.0]-non-5-en, 1,8-diazabicyclo-[5.4.0]-undec-7-en, 1,4-diazabicyclooctane, tetramethylhexamethylendiamine, tetramethylethylendiamine, tetramethylpropylendiamine, tetramethylbutylendiamine, 1,2-dimorpholylethan, pentamethyldiethyltriamine, pentaethyldiethylentriamine, pentamethyldipropylentriamine, tetramethyldiaminomethane, tetrapropyldiaminomethane, hexamethyltriethylentetramine, hexamethyltripropylenetetramine, diisobutylentriamine, tri-isopro-pylentriamine, and mixtures thereof.

Acetoacetamide Salt Formation Reaction

Once formed in reaction (1), the sulfamic acid salt is reacted with the acetoacetylating agent to form the acetoacetamide salt, preferably acetoacetamide-N-sulfonate triethylammonium salt. Preferably, the acetoacetylating agent comprises diketene, although other acetoacetylating agents may be employed, either with or without diketene.

In one embodiment, the resultant acetoacetamide salt corresponds to the following formula (3).

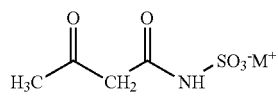
(3)

wherein $M^+$ is an appropriate ion. Preferably, $M^+$ is an alkali metal ion or $N^+R_1R_2R_3R_4$. $R_1$, $R_2$, $R_3$ and $R_4$, independently of one another, may be organic radicals or hydrogen, preferably H or $C_1$-$C_8$ alkyl, $C_6$-$C_{10}$ cycloalkyl, aryl and/or aralkyl. In a preferred embodiment, $R_1$ is hydrogen, and $R_2$, $R_3$ and $R_4$ are alkyl, e.g., ethyl.

An exemplary reaction scheme for forming an acetoacetamide salt employs a trialkyl ammonium amidosulfamic acid salt and diketene as reactants and yields an acetoacetamide triethylammonium salt is shown in reaction (4), below.

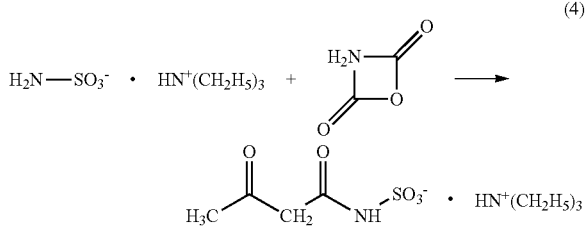
(4)

In one embodiment, the reaction is conducted in the presence of a catalyst, which may vary widely. In some embodiments, the catalyst comprises one or more amines and/or phosphines. Preferably, the catalyst comprises triethylamine. In some cases trimethylamine serves as both a catalyst and a reactant.

In one embodiment, wherein the amidosulfamic acid salt formation reaction and the acetoacetamide salt formation reaction are conducted in separate reactors, a second reaction mixture comprises the amidosulfamic acid salt, the diketene, and the catalyst, e.g., triethylamine. Preferably, catalyst from the first reaction is carried through to the reaction mixture of the second reaction. The second reaction mixture is then subjected to conditions effective to form the acetoacetamide salt.

In one embodiment, the composition of the second reaction mixture may be similar to that of the first reaction mixture. In a preferred embodiment, the reaction product of the amidosulfamic acid salt formation reaction provides the amidosulfamic acid salt component of the second reaction mixture. In addition to the above-mentioned components, the second reaction mixture may further comprise reaction by-products from the first reaction or non-reacted starting materials.

In one embodiment, the amount of acetoacetylating agent, e.g., diketene, should be at least equimolar to the reactant amidosulfamic acid salt that is provided. In one embodiment, the process may utilize a diketene excess less than 30 mol %, e.g., less than 10 mol %. Greater excesses are also contemplated.

The amidosulfamic acid salt formation reaction and/or the acetoacetamide salt formation reaction may employ an organic solvent. Suitable inert organic solvents include any organic solvents that do not react in an undesired manner with the starting materials, cyclizing agent, final products and/or the catalysts in the reaction. The solvents preferably have the ability to dissolve, at least partially, amidosulfamic acid salts. Exemplary organic solvents include halogenated aliphatic hydrocarbons, preferably having up to 4 carbon atoms such as, for example, methylene chloride, chloroform, 1,2-dichlorethane, trichloroethylene, tetrachloroethylene, trichlorofluoroethylene; aliphatic ketones, preferably those having 3 to 6 carbon atoms such as, for example, acetone, methyl ethyl ketone; aliphatic ethers, preferably cyclic aliphatic ethers having 4 or 5 carbon atoms such as, for example, tetrahydrofuran, dioxane; lower aliphatic carboxylic acids, preferably those having 2 to 6 carbon atoms such as, for example, acetic acid, propionic acid; aliphatic nitriles, preferably acetonitrile; N-alkyl-substituted amides of carbonic acid and lower aliphatic carboxylic acids, preferably amides having up to 5 carbon atoms such as, for example, tetramethylurea, dimethylformamide, dimethylacetamide, N-methylpyrrolidone; aliphatic sulfoxides, preferably dimethyl sulfoxide, and aliphatic sulfones, preferably sulfolane.

Particularly preferred solvents include dichloromethane (methylene chloride), 1,2-dichloroethane, acetone, glacial acetic acid and dimethylformamide, with dichloromethane (methylene chloride) being particularly preferred. The solvents may be used either alone or in a mixture. In one embodiment, the solvent is a halogenated, aliphatic hydrocarbon solvent, preferably the solvent is dichloromethane. Chloroform and tetrachloromethane are also exemplary solvents.

In one embodiment, the acetoacetamide salt formation reaction is conducted a temperature ranging from −30° C. to 50° C., e.g., from 0° C. to 25° C. The reaction pressure may vary widely. In preferred embodiments, the reaction is carried out at atmospheric pressure, although other pressures are also contemplated. The reaction time may vary widely, preferably ranging from 0.5 hours to 12 hours, e.g., from 1 hour to 10 hours. In one embodiment, the reaction is carried out by introducing the amidosulfamic acid salt and metering in the diketene. In another embodiment, the reaction is carried out by introducing diketene and metering in the amidosulfamic acid salt. The reaction may be carried out by introducing the diketene and amidosulfamic acid and metering in the catalyst.

Once formed, each reaction product is optionally subjected to one or more purification steps. For example the solvent may be separated from the reaction product, e.g., via distillation, and the residue (mainly acetoacetamide-N-sulfonate) may be recrystallized from a suitable solvent such as, for example, acetone, methyl acetate or ethanol.

Cyclization and Hydrolyzation

The acetoacetamide salt is reacted with cyclizing agent, e.g., cyclizing agent in the cyclizing agent composition, in the presence of a solvent to form the cyclic (sulfur trioxide) adduct composition, which contains cyclic sulfur trioxide adduct and, in some cases, impurities. In some cases, a cooling step occurs before the cyclic sulfur trioxide adduct formation reaction. In one embodiment, the cyclization is achieved by using at least an equimolar amount of the cyclizing agent. The cyclizing agent may be dissolved in an inert inorganic or organic solvent. The cyclizing agent is generally used in a molar excess, e.g., up to a 20 fold excess, or up to a 10 fold excess, based on the total moles of acetoacetamide salt. An exemplary cyclization reaction using sulfur trioxide as the cyclizing agent is shown in reaction (5), below.

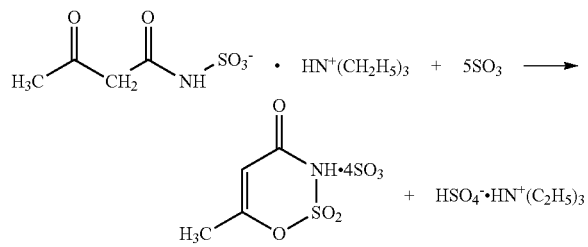

(5)

In one embodiment, the weight ratio of solvent to cyclizing agent in the cyclizing agent composition is at least 1:1, e.g., at least 2:1, or at least 5:1. In one embodiment, the weight ratio of solvent to cyclizing agent in the cyclizing agent composition ranges from 1:1 to 25:1, e.g., from 1:1 to 10:1, from 2:1 to 10:1, or from 5:1 to 10:1.

A cyclizing agent may be any compound that initiates the ring closure of the acetoacetamide salt. Although sulfur trioxide is a preferred cyclizing agent, the employment of other cyclizing agents is contemplated.

The cyclizing agent may be added to the reaction mixture either in the solid or the liquid form or by condensing in vapor. Suitable inert inorganic or organic solvents are those liquids which do not react in an undesired manner with sulfur trioxide or the starting materials or final products of the reaction. Preferred organic solvents include, but are not limited to, halogenated aliphatic hydrocarbons, preferably having up to four carbon atoms, such as, for example, methylene chloride (dichloromethane), chloroform, 1,2-dichloroethane, trichloroethylene, tetrachloroethylene, trichlorofluoroethylene; esters of carbonic acid with lower aliphatic alcohols, preferably with methanol or ethanol; nitroalkanes, preferably having up to four carbon atoms, in particular nitromethane; alkyl-substituted pyridines, preferably collidine; and aliphatic sulfones, preferably sulfolane. Particularly preferred solvents for the cyclization reaction include dichloromethane (methylene chloride), 1,2-dichloroethane, acetone, glacial acetic acid and dimethylformamide, with dichloromethane (methylene dichloride) being particularly preferred. Other solvents, e.g., other solvents mentioned herein, may also be suitable as solvents. The solvents may be used either alone or in a mixture. In one embodiment, the solvent is a halogenated, aliphatic hydrocarbon solvent, preferably the solvent is dichloromethane. The processes may employ these solvents alone or in mixtures thereof.

In some cases, the solvent in the cyclizing agent composition may be selected from 1) concentrated sulfuric acid, 2) liquid sulfur dioxide, or 3) an inert organic solvent.

In a preferred embodiment, the same solvent is used in both the acetoacetamide salt formation reaction and the cyclization reaction. As one benefit, the solution obtained in the acetoacetamide salt formation reaction, without isolation of the acetoacetamide salt formation reaction product, may be used immediately in the cyclization.

In one embodiment, the reaction temperature for the cyclization reaction ranges from −70° C. to 175° C., e.g., from −40° C. to 60° C. The pressure at which the reaction is conducted may vary widely. In one embodiment, the reaction is conducted at a pressure ranging from 0.01 MPa to 10 MPa, e.g., from 0.1 MPa to 5 MPa. Preferably, the reaction is conducted at atmospheric pressure.

The acetoacetamide salt may be introduced to the cyclization reactor and the cooled cyclizing agent composition, e.g., a solution of cyclizing agent optionally in solvent, may be metered into the reactor. In preferred embodiments, both reactants (acetoacetamide salt and cyclizing agent) are simultaneously fed into the reactor. In one embodiment, the cooled cyclizing agent composition is initially introduced into the reactor and the acetoacetamide salt is added. Preferably, at least part of the cyclizing agent composition is introduced into the reactor and, either continuously or in portions, acetoacetamide salt and (additional) cyclizing agent are then metered in, preferably while maintaining the temperature as described above.

The acetoacetamide salt may be introduced to the reactor and the cyclizing agent composition may be metered into the reactor. In preferred embodiments, both reactants are simultaneously fed into the reactor. In one embodiment, the cyclizing agent composition is initially introduced into the reactor and the acetoacetamide salt is added. Preferably, at least part of the cyclizing agent composition is introduced into the reactor and, either continuously or in portions, acetoacetamide salt and (additional) cyclizing agent are then metered in, preferably while maintaining the temperature as described above.

The formation of the crude acesulfame potassium composition from the cyclic sulfur trioxide adduct composition, in some embodiments, comprises the steps of hydrolyzing the cyclic sulfur trioxide adduct to form an acesulfame-H composition; neutralizing the acesulfame-H in the acesulfame H composition to form a crude acesulfame potassium composition; and forming the acesulfame potassium composition from the crude acesulfame potassium composition.

The cyclic sulfur trioxide adduct may be hydrolyzed via conventional means, e.g., using water. Thus, the forming step may comprise the steps of hydrolyzing the cyclic sulfur trioxide adduct to form an acesulfame-H composition. Acesulfame-H is referred to as sweetener acid.

An exemplary hydrolysis reaction scheme is shown in reaction (6), below.

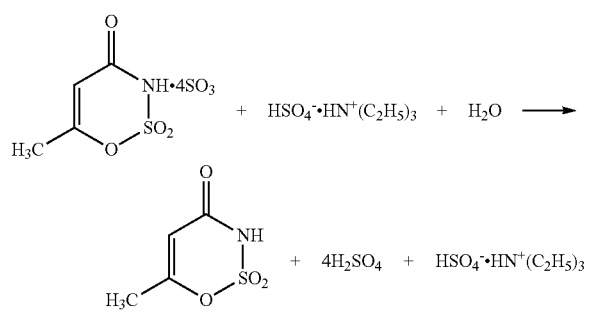

(6)

The addition of the water leads to a phase separation. The majority of the sweetener acid, acesulfame-H (6-methyl-3, 4-dihydro-1,2,3-oxathiazin-4-one 2,2-dioxide), which is formed via the hydrolysis, is present in the organic phase, e.g., at least 60 wt %, at least 70%, at least 80%, or at least 90%. The remainder of the sweetener acid is in the water phase and can be extracted and optionally added to the sweetener acid in the organic phase. In cases where dichloromethane is used as the reaction medium, water or ice may be added, e.g., in a molar excess, based on the sulfur trioxide, to the cyclic sulfur trioxide adduct/sulfur trioxide solution.

In some cases, the hydrolysis step comprises adding water to the cyclic sulfur trioxide adduct. In preferred embodiments, the weight ratio of water to acetoacetamide salt is greater than 1.3:1, e.g., greater than 1.5:1, greater than 1.7:1, greater than 2:1 or greater than 2.2:1. Employment of these ratios may lead to decreases in acetoacetamide-N-sulfonic acid and/or acetoacetamide formation in the neutralized crude acesulfame potassium composition, e.g., the crude acesulfame potassium composition may comprise acetoacetamide-N-sulfonic acid in the amounts discussed herein.

After the addition of water, the reaction solvent, e.g., dichloromethane, may be removed by distillation, or the acesulfame-H that remains in the organic phase may be extracted with a more suitable solvent. Suitable solvents are those which are sufficiently stable towards sulfuric acid and which have a satisfactory dissolving capacity. Other suitable solvents include esters of carbonic acid such as, for example dimethyl carbonate, diethyl carbonate and ethylene carbonate, or esters of organic monocarboxylic acids such as, for example, isopropyl formate and isobutyl formate, ethyl acetate, isopropyl acetate, butyl acetate, isobutyl acetate and neopentyl acetate, or esters of dicarboxylic acids or amides which are immiscible with water, such as, for example, tetrabutylurea, are suitable. Isopropyl acetate and isobutyl acetate are particularly preferred.

The combined organic phases are dried with, for example, $Na_2SO_4$, and are evaporated. Any sulfuric acid which has been carried over in the extraction may be removed by appropriate addition of aqueous alkali to the organic phase. For this purpose, dilute aqueous alkali may be added to the organic phase until the pH reached in the aqueous phase corresponds to that of pure 6-methyl-3,4-dihydro1,2,3-oxathiazin-4-one 2,2-dioxide at the same concentration in the same two-phase system of extracting agent and water.

Neutralization

The neutralization of the acesulfame-H yields a non-toxic salt of acesulfame-H, e.g., acesulfame potassium. In one embodiment, neutralization is carried out by reacting the acesulfame-H with an appropriate base, e.g., potassium hydroxide, in particular a membrane-produced potassium hydroxide. Other suitable bases include, for example, KOH, $KHCO_3$, $K_2CO_3$, and potassium alcoholates. An exemplary reaction scheme using potassium hydroxide as a neutralizing agent is shown in reaction (7), below.

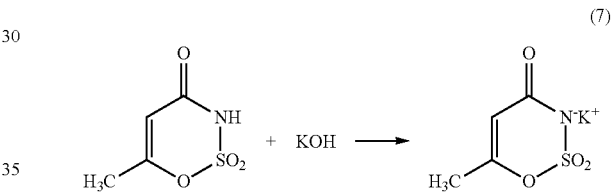

(7)

In one embodiment, the acesulfame-H may be neutralized and extracted directly from the purified organic extraction phase using an aqueous potassium base. The acesulfame potassium then precipitates out, where appropriate after evaporation of the solution, in the crystalline form, and it can also be recrystallized for purification.

In one embodiment, the process is not a small-scale batch process or a laboratory-scale process. For example, the inventive process for producing a finished acesulfame potassium composition may yield at least 50 grams of finished acesulfame potassium composition per batch, e.g., at least 100 grams per batch, at least 500 grams per batch, at least 1 kilogram per batch, or at least 10 kilograms per batch. In terms of rates, the inventive process may yield at least 50 grams of finished acesulfame potassium composition per hour, e.g., at least 100 grams per hour, at least 500 grams per hour, at least 1 kilogram per hour, or at least 10 kilograms per hour.

FIG. 1 shows an exemplary acesulfame potassium process 100 in accordance with the process described herein. Process 100 comprises amidosulfamic acid salt formation reactor 102 and acetoacetamide salt formation reactor 104. Although FIG. 1 shows separate reactors for the two intermediate formation reactions, other configurations, e.g., a one reactor process, are within the contemplation of the present process. Sulfamic acid is fed to amidosulfamic acid salt formation reactor 102 via sulfamic acid feed line 106. Amine(s), preferably triethylamine, are fed to amidosulfamic acid salt formation reactor 102 via amine feed line 108. In addition to sulfamic acid and amine(s), acetic acid is also fed to amidosulfamic acid salt formation reactor 102 (via feed line 110). The resultant reaction mixture in amidosulfamic acid salt formation reactor 102 is as discussed above. In amidosulfamic acid salt formation reactor 102, the sulfamic acid and the amine (in the presence of the acetic acid) are reacted to yield a crude amidosulfamic acid salt composition, which exits reactor 102 via line 112. Although not shown, a reaction solvent, e.g., dichloromethane may also be present in the amidosulfamic acid salt formation reactor 102.

The crude amidosulfamic acid salt composition in line 112 is directed to acetoacetamide salt formation reactor 104. Diketene is fed to acetoacetamide salt formation reactor 104 via feed line 114. In acetoacetamide salt formation reactor 104, the amidosulfamic acid salt and the diketene are reacted to yield a crude acetoacetamide salt composition, which exits reactor 104 via line 118. Although not shown, dichloromethane may also be present in the acetoacetamide salt formation reactor 104.

Cyclizing agent (sulfur dioxide) and solvent (dichloromethane) are fed to vessel 119 via feed lines 121 and 123. Vessel 119 is preferably a vessel wherein a cyclizing agent composition comprising these two components is formed. The cyclizing agent composition comprising both cyclizing agent and solvent exits vessel 119 via line 125.

The crude acetoacetamide salt composition is directed to cyclization reactor 120 via line 118. The cyclizing agent composition is also directed to cyclization reactor 120 (via line 125). Line 125 is preferably made of a material and in such a size and shape to facilitate the residence times discussed herein. In cyclization reactor 120, the acetoacetamide salt in the crude acetoacetamide salt composition in line 118 is cyclized and a cyclic sulfur trioxide adduct stream exits via line 124.

The cyclic sulfur trioxide adduct in line 124, is directed to hydrolysis reactor 126. Water is fed to hydrolysis reactor 126 via water feed 128. In hydrolysis reactor 126, the cyclic sulfur trioxide adduct is hydrolyzed to yield a crude acesulfame-H composition, which exits hydrolysis reactor 126 via line 130 and is directed to phase separation unit 132. Phase separation unit 132 separates the contents of line 130 into organic phase 134 and aqueous phase 136. Organic phase 134 comprises a major amount of the acesulfame-H in line 130 as well as solvent, e.g., methylene chloride. Aqueous phase 136 exits via line 137 and comprises triethylammonium sulfate, and optionally sulfuric acid and minor amounts of acesulfame-H. The aqueous phase may be further purified to separate and/or recover the acesulfame-H and/or the triethylammonium sulfate. The recovered acesulfame-H may be combined with the acesulfame from the organic phase (not shown).

Organic phase 134 exits phase separation unit 132 and is directed to extraction column 138 (via line 140). Water is fed to extraction column 138 via water feed 142. The water extracts residual sulfates from the contents of line 140 and a purified acesulfame-H composition exits extraction column 138 via line 144. The extracted sulfates exit extraction column 138 via line 145.

The purified acesulfame-H composition in line 144 is directed to neutralization unit 146. Potassium hydroxide is also fed to neutralization unit 146 (via line 148). The addition of the potassium hydroxide (via line 148) to neutralization unit 146 may be adjusted to achieve and/or maintain the desired pH levels during the neutralization, as discussed herein. The potassium hydroxide neutralizes the acesulfame-H in the purified acesulfame-H composition to yield a product comprising acesulfame potassium, dichloromethane, water, potassium hydroxide, and impurities, e.g., acetoacetamide-N-sulfonic acid or acetoacetamide, which exits neutralization unit 146 via line 150. This product may be considered a crude acesulfame potassium composition.

The crude acesulfame potassium product stream in line 150 may be directed to treatment zone 156 to recover finished acesulfame potassium, which is shown exiting via stream 152. In addition to the finished acesulfame potassium, dichloromethane and potassium hydroxide may be separated from the crude acesulfame potassium product stream, as shown by stream 154. The contents of stream 154 may be recovered and/or recycled to the process. Treatment zone 156 may comprise one or more of the treatment operations described herein, e.g., stripping, evaporation, crystallization, and filtration.

The product in line 150 is directed to phase separation unit 160. Phase separation unit 160 separates the product in line 150 into organic phase 162 and an aqueous phase 164. Aqueous phase 164 comprises a major amount of the acesulfame potassium in line 150 as well as some impurities. Organic phase 162 comprises potassium hydroxide, dichloromethane, and water and may be further treated to recover these components. Aqueous phase 164 (without any further treatment) may be considered a crude acesulfame potassium composition. Aqueous phase 164 may be optionally treated to form a finished acesulfame potassium composition.

Aqueous phase 164 is directed to treatment unit 156 via line 166. In treatment unit 156, aqueous phase 164 is treated to obtain finished acesulfame potassium composition (product that may be sold), which is shown exiting via stream 152. In addition to the finished acesulfame potassium composition, dichloromethane and potassium hydroxide may be separated. These components exit treatment unit 156 via line 154. The contents of stream 154 may be recovered and/or recycled to the process.

The invention relates also to the following aspects:

Aspect 1: A process for producing a finished acesulfame potassium composition, the process comprising the steps of:
(a) forming a cyclic sulfur trioxide adduct;
(b) hydrolyzing the cyclic sulfur trioxide adduct to form an acesulfame-H composition comprising acesulfame-H;
(c) neutralizing the acesulfame-H in the acesulfame-H composition to form a crude acesulfame potassium composition comprising acesulfame potassium and less than 2800 wppm acetoacetamide-N-sulfonic acid, wherein the neutralizing step is conducted at a pH at or below 11.0; and
(d) treating the crude acesulfame potassium composition to form the finished acesulfame potassium composition comprising acesulfame potassium and less than 37 wppm acetoacetamide-N-sulfonic acid.

Aspect 2: The process of aspect 1, wherein the neutralization step comprises
reacting acesulfame-H with a neutralizing agent in an acesulfame-H/neutralizing agent reaction mixture to form the acesulfame potassium composition.

Aspect 3: The process of any one of the preceding aspects, wherein the neutralizing agent comprises potassium hydroxide.

Aspect 4: The process of any one of the preceding aspects, wherein the potassium hydroxide is produced via a membrane process and the finished acesulfame potassium composition less than 10 wppm mercury.

Aspect 5: The process of any one of the preceding aspects, wherein the acesulfame-H/neutralizing agent reaction mixture comprises from 1 wt % to 95 wt % neutralizing agent and from 1 wt % to 95 wt % acesulfame-H, based on the total weight of the acesulfame-H/neutralizing agent reaction mixture.

Aspect 6: The process of any one of the preceding aspects, wherein the neutralizing step (c) comprises neutralizing the acesulfame-H in the acesulfame-H composition to form the crude acesulfame potassium composition further comprising acetoacetamide.

Aspect 7: The process of any one of the preceding aspects, wherein the crude acesulfame potassium composition comprises from 500 wppm to 2375 wppm acetoacetamide-N-sulfonic acid and the finished acesulfame potassium composition comprises less than 25 wppm acetoacetamide-N-sulfonic acid and further comprises less than 25 wppm acetoacetamide.

Aspect 8: The process of any one of the preceding aspects, wherein the neutralizing step (c) is conducted at a pH ranging from 9.0 to 11.0 and the crude acesulfame potassium composition comprises from 20 wppm to 2500 wppm acetoacetamide-N-sulfonic acid and the finished acesulfame potassium composition comprises less than 25 wppm acetoacetamide-N-sulfonic acid and less than 15 wppm acetoacetamide.

Aspect 9: The process of any one of the preceding aspects, wherein the neutralizing step (c) is conducted at a pH ranging from 8 to 10.3 and the crude acesulfame potassium composition comprises from 600 wppm to 1200 wppm acetoacetamide-N-sulfonic acid, and the finished acesulfame potassium composition comprises less than 10 wppm acetoacetamide-N-sulfonic acid and less than 10 wppm acetoacetamide.

Aspect 10: The process of any one of the preceding aspects, wherein the neutralizing step (c) is conducted at a pH ranging from 8 to 10.3 and the crude acesulfame potassium composition comprises less than 2400 wppm acetoacetamide-N-sulfonic acid, and the finished acesulfame potassium composition comprises less than 10 wppm acetoacetamide-N-sulfonic acid and less than 10 wppm acetoacetamide.

Aspect 11: The process of any one of the preceding aspects, wherein the finished acesulfame potassium composition comprises less than 37 wppm acetoacetamide.

Aspect 12: The process of any one of the preceding aspects, wherein the neutralizing step (c) is conducted at a pH ranging from 9.0 to 11.0.

Aspect 13: The process of any one of the preceding aspects, wherein the neutralizing step (c) is conducted at a pH ranging from 9.0 to 10.5.

Aspect 14: The process of any one of the preceding aspects, wherein the neutralizing step (c) is conducted at a pH ranging from 8.0 to 10.3.

Aspect 15: The process of any one of the preceding aspects, wherein the treating step (d) is conducted at a temperature below 90° C.

Aspect 16: The process of any one of the preceding aspects, wherein the treating step (d) comprises an evaporating step with a residence time less than 180 minutes.

Aspect 17: The process of any one of the preceding aspects, wherein the neutralizing step is maintained at a pH at or below 11.0.

Aspect 18: A finished acesulfame potassium composition produced or producible by, or obtainable or obtained from the process of any one of aspects 1 to 17.

Aspect 19: A process for producing a finished acesulfame potassium composition, the process comprising the steps of:
(a) reacting sulfamic acid and triethylamine to form an amidosulfamic acid salt;
(b) reacting the amidosulfamic acid salt and diketene to form acetoacetamide salt;
(c) contacting dichloromethane and a sulfur trioxide to form a cyclizing agent composition;
(d) reacting the acetoacetamide salt with sulfur trioxide in the cyclizing agent composition to form a cyclic sulfur trioxide adduct;
(e) hydrolyzing the cyclic sulfur trioxide adduct to form an acesulfame-H composition comprising acesulfame-H;
(f) neutralizing the acesulfame-H in the acesulfame-H to form a crude acesulfame potassium composition comprising acesulfame potassium and less than 2800 wppm acetoacetamide-N-sulfonic acid, wherein neutralizing step is conducted at a pH at or below 11.0,
(g) treating the crude acesulfame potassium composition to form the finished acesulfame potassium composition comprising acesulfame potassium and less than 37 wppm acetoacetamide-N-sulfonic acid,
wherein steps (a), (b), and (c) can be performed in any order before the performance of step (d).

Aspect 20: The process of aspect 19, wherein the finished acesulfame potassium composition further comprises less than 20 wppm acetoacetamide.

Aspect 21: The process of any one of the preceding aspects, wherein the neutralizing step (f) is conducted at a pH ranging from 9.0 to 11.0 and the crude acesulfame potassium composition comprises from 20 wppm to 2500 wppm acetoacetamide-N-sulfonic acid and the finished acesulfame potassium composition comprises less than 25 wppm acetoacetamide-N-sulfonic acid and less than 15 wppm acetoacetamide.

Aspect 22: An acesulfame potassium composition comprising acesulfame potassium and less than 25 wppm acetoacetamide-N-sulfonic acid and less than 25 wppm acetoacetamide.

Aspect 23: The acesulfame potassium composition of aspect 22, further comprising 0.001 wppm to 5 wppm organic impurities and/or 0.001 wppm to 5 wppm of at least one heavy metal.

Aspect 24: The acesulfame potassium composition of any one of the preceding aspects, wherein the at least one heavy metal is selected from the group consisting of mercury, lead and mixtures thereof.

Aspect 25: The acesulfame potassium composition of any one of the preceding aspects, wherein the mercury is present in an amount of 1 wppb to 20 wppm.

Aspect 26: The acesulfame potassium composition of any one of the preceding aspects, wherein the lead is present in an amount of 1 wppb to 25 wppm.

EXAMPLES

The following examples are included to illustrate the process and compositions and are not meant to limit the scope of the application.

Example 1 a-c and Comparative Example A 100 mmol of 99.5% pure sulfamic acid was suspended in 50 mL dichloromethane in a flask with reflux. Under continuous agitation, 105 mmol of trimethylamine was added within approximately 3 minutes. During this time, temperature increased due to acid/base exothermal reaction up to about 42° C. (the boiling point of dichloromethane). This first reaction mixture was stirred for approximately 15 additional minutes, until no solid sedimentation was seen in the flask. Then, 10 mmol of acetic acid was added to the first reaction mixture and was stirred for approximately 15 additional minutes. At this point, within 7 minutes of the addition of the acetic acid, 110 mmol of diketene was added dropwise to form a second reaction mixture. After the addition of all of the diketene was added to the second reaction mixture and approximately 15 minutes of reaction time, this second reaction mixture was cooled. The resultant cooled second reaction mixture contained approximately 30% acetoacetamide N-sulfonate triethylammonium salt. Additional batches of cooled second reaction mixture were prepared as necessary.

In a separate vessel, a sulfur trioxide/dichloromethane composition comprising approximately 15 wt % sulfur trioxide and approximately 85 wt % dichloromethane was prepared by contacting the two components with one another.

A second flask (a 4 necked round bottom flask equipped with mechanical stirrer, thermometer, and feed vessels) was placed into a cooling bath containing a mixture of isopropanol and dry ice. Approximately 200 g of the acetoacetamide-N-sulfonate triethylammonium salt solution and approximately 577 g of the sulfur trioxide/dichloromethane compositions were measured. Approximately 15 wt % of the total sulfur trioxide/dichloromethane composition (approximately 87 g) was initially fed to the reaction flask under continuous agitation by mechanical stirrer. When the temperature of the flask contents reached −35° C. (due to the cooling batch), the remainder of the sulfur trioxide/dichloromethane composition and all of the acetoacetamide-N-sulfonate triethylammonium salt solution were fed into the second flask. The time period that the solvent contacts the cyclizing agent before formation of the cyclic sulfur trioxide adduct, e.g., before the acetoacetamide-N-sulfonate triethylammonium salt solution was fed to the second flask, was less than an hour. The feed rate was controlled in such a way that the temperature of the second flask contents remained between −25° and −35° C. during the feeding/cyclization reaction. After the reactants were fed, the reaction was allowed to proceed for approximately one additional minute. The cooling bath was then removed.

After approximately one minute, the temperature of the flask contents reached approximately −22° C. At this time, hydrolysis was initiated by feeding deionized water to the flask. Water was fed over 10 minutes. The hydrolysis reaction was exothermic. Water was added slowly so as to maintain temperature between −20° C. and −5° C. After addition of water, reaction mixture was allowed to reach room temperature.

The weight ratio of water added for hydrolysis to the acetoacetamide-N-sulfonate triethylammonium salt in dichloromethane solution was kept constant for Examples 1 a-c and Comparative Example A.

The hydrolyzed product was phase separated via a separating funnel. A heavier organic sweetener acid-dichloromethane phase (acesulfame-H composition) was separated out, and the remaining aqueous phase was discarded.

The acesulfame-H in the acesulfame-H composition was neutralized with a 10% potassium hydroxide solution. Neutralization was carried out at 25° C.±1° C. Potassium hydroxide addition was completed within 20 minutes. The neutralization was conducted at various pH levels as shown in Table 1.

After completion of the neutralization step, an additional phase separation was performed using a separating funnel to yield an aqueous phase containing acesulfame potassium (and some impurities) and an organic phase. The aqueous phase is considered a crude acesulfame potassium composition in Table 1. The remaining dichloromethane in the organic phase was discarded.

The crude acesulfame potassium samples of Examples 1 a-c and Comparative Example A were tested for acetoacetamide-N-sulfonic acid content. Testing was performed using the HPLC equipment and techniques discussed herein. In particular, the HPLC analysis was performed using an LC Systems HPLC unit from Shimadzu having a CBM-20 Shimadzu controller and being equipped with an IonPac NS1 ((5 μm) 150×4 mm) analytical column and an IonPac NG1 guard column (35×4.0 mm). A Shimadzu SPD-M20A photodiode array detector was used for detection (at 270 nm and 280 nm wavelength). Analysis was performed at 23° C. column temperature. As a first eluent solution, an aqueous mixture of tetra butyl ammonium hydrogen sulfate (3.4 g/L), acetonitrile (300 mL/L), and potassium hydroxide (0.89 g/L) was employed; as a second eluent solution, an aqueous mixture of tetra butyl ammonium hydrogen sulfate (3.4 g/L) and potassium hydroxide (0.89 g/L) was employed. Elution was conducted in gradient mode according to the following second eluent flow profile:

0 to 3 minutes: constant 80% (v/v)
3 to 6 minutes: linear reduction to 50% (v/v)
6 to 15 minutes: constant at 50% (v/v)
15 to 18 minutes: linear reduction to 0%
18 to 22 minutes: constant at 0%
22 to 24 minutes: linear increase to 80% (v/v)
24 to 35 minutes constant at 80% (v/v).

Overall flow rate of eluent was approximately 1.2 mL/min. The data collection and calculations were performed using Lab Solution software from Shimadzu.

The results are shown in Table 1.

TABLE 1

Acetoacetamide-N-sulfonic Acid Content in Crude Acesulfame Potassium Compositions

| Ex./Comp. Ex. | pH | Acetoacetamide-N-sulfonic acid, wppm |
| --- | --- | --- |
| Example 1a | 9 | 1538 |
| Example 1b | 9.8 | 1954 |
| Example 1c | 11 | 2361 |
| Comp. Ex. A | 12 | 3066 |

As shown in Table 1, when the neutralizing step is conducted at a pH at or below 11.0, the acetoacetamide-N-sulfonic acid contents in the resultant crude acesulfame potassium compositions are significantly lower than when higher pH is employed—minimally 23% less (Comparative Example A versus Example 1c 3066-2361/3066=23%).

Importantly, the reduction of acetoacetamide-N-sulfonic acid content in the crude acesulfame potassium composition provides for accompanying reductions in acetoacetamide formation (for example via acetoacetamide-N-sulfonic acid degradation) in subsequent separation operations, which leads to reduced acetoacetamide content in the resultant finished acesulfame potassium composition.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing a finished acesulfame potassium composition, the process comprising the steps of:
   (a) forming a cyclic sulfur trioxide adduct;
   (b) hydrolyzing the cyclic sulfur trioxide adduct to form an acesulfame-H composition comprising acesulfame-H;
   (c) neutralizing the acesulfame-H in the acesulfame-H composition to form a crude acesulfame potassium composition, wherein the neutralizing step is conducted at a pH at or below 11.0; and
   (d) treating the crude acesulfame potassium composition to form a finished acesulfame potassium composition comprising acesulfame potassium and less than 37 wppm acetoacetamide-N-sulfonic acid.

2. The process of claim 1, wherein the neutralizing step (c) comprises:
   reacting acesulfame-H with a neutralizing agent in an acesulfame-H/neutralizing agent reaction mixture to form the acesulfame potassium composition.

3. The process of claim 2, wherein the neutralizing agent comprises potassium hydroxide.

4. The process of claim 3, wherein the potassium hydroxide is produced via a membrane process and the finished acesulfame potassium composition comprises less than 10 wppm mercury.

5. The process of claim 2, wherein the acesulfame-H/neutralizing agent reaction mixture comprises from 1 wt % to 95 wt % neutralizing agent and from 1 wt % to 95 wt % acesulfame-H, based on the total weight of the acesulfame-H/neutralizing agent reaction mixture.

6. The process of claim 1, wherein the neutralizing step (c) is conducted at a pH ranging from 9.0 to 11.0.

7. The process of claim 1, wherein the neutralizing step (c) is conducted at a pH ranging from 9.0 to 10.5.

8. The process of claim 1, wherein the neutralizing step (c) is conducted at a pH ranging from 8.0 to 10.3.

9. The process of claim 1, wherein the treating step (d) is conducted at a temperature below 90° C.

10. The process of claim 1, wherein the treating step (d) comprises an evaporating step with a residence time less than 180 minutes.

11. The process of claim 1, wherein the neutralizing step is maintained at a pH at or below 11.0.

12. The process of claim 1, wherein the cyclic sulfur trioxide adduct is formed by a process that comprises (a) reacting sulfamic acid and triethylamine to form an amidosulfamic acid salt; (b) reacting the amidosulfamic acid salt and diketene to form acetoacetamide salt; (c) contacting dichloromethane and a sulfur trioxide to form a cyclizing agent composition; and (d) reacting the acetoacetamide salt with sulfur trioxide in the cyclizing agent composition to form the cyclic sulfur trioxide adduct.

13. The process of claim 1, wherein the finished acesulfame potassium composition comprises less than 37 wppm acetoacetamide.

14. The process of claim 1, wherein the finished acesulfame potassium composition comprises less than 25 wppm acetoacetamide.

15. The process of claim 1, wherein the finished acesulfame potassium composition comprises less than 20 wppm acetoacetamide.

16. The process of claim 1, wherein the finished acesulfame potassium composition comprises less than 25 wppm acetoacetamide-N-sulfonic acid.

17. The process of claim 1, wherein the finished acesulfame potassium composition comprises less than 10 wppm acetoacetamide-N-sulfonic acid.

18. The process of claim 1, wherein the finished acesulfame potassium composition comprises less than 25 wppm acetoacetamide-N-sulfonic acid and comprises less than 25 wppm acetoacetamide.

19. The process of claim 1, wherein the finished acesulfame potassium composition comprises less than 25 wppm acetoacetamide-N-sulfonic acid and less than 15 wppm acetoacetamide.

20. The process of claim 1, wherein the finished acesulfame potassium composition comprises less than 10 wppm acetoacetamide-N-sulfonic acid and less than 10 wppm acetoacetamide.

21. The process of claim 1, wherein the crude acesulfame potassium composition comprises acetoacetamide, acetoacetamide-N-sulfonic acid, or a combination thereof.

22. The process of claim 1, wherein the crude acesulfame potassium composition comprises less than 2800 wppm acetoacetamide-N-sulfonic acid.

23. The process of claim 1, wherein the crude acesulfame potassium composition comprises from 500 wppm to 2375 wppm acetoacetamide-N-sulfonic acid.

24. The process of claim 1, wherein the neutralizing step (c) is conducted at a pH ranging from 9.0 to 11.0 and the finished acesulfame potassium composition comprises less than 25 wppm acetoacetamide-N-sulfonic acid and less than 15 wppm acetoacetamide.

25. The process of claim 1, wherein the neutralizing step (c) is conducted at a pH ranging from 8 to 10.3 and the finished acesulfame potassium composition comprises less than 10 wppm acetoacetamide-N-sulfonic acid and less than 10 wppm acetoacetamide.

26. The process of claim 1, wherein the neutralizing step (c) is conducted at a pH ranging from 8 to 10.3 and the finished acesulfame potassium composition comprises less than 10 wppm acetoacetamide-N-sulfonic acid and less than 10 wppm acetoacetamide.

* * * * *